(12) United States Patent
Rost

(10) Patent No.: US 9,956,026 B2
(45) Date of Patent: May 1, 2018

(54) BLOOD VESSEL CAUTERIZING TOOL ASSEMBLY

(71) Applicant: Virginia Rost, Mesa, AZ (US)

(72) Inventor: Virginia Rost, Mesa, AZ (US)

( * ) Notice: Subject to any disclaimer, the term of this patent is extended or adjusted under 35 U.S.C. 154(b) by 501 days.

(21) Appl. No.: 14/620,439

(22) Filed: Feb. 12, 2015

(65) Prior Publication Data
US 2016/0235466 A1 Aug. 18, 2016

(51) Int. Cl.
| | | |
|---|---|---|
| A61B 18/18 | (2006.01) |
| A61B 18/08 | (2006.01) |
| A61B 18/00 | (2006.01) |
| A61B 90/30 | (2016.01) |
| A61B 18/10 | (2006.01) |
| A61B 18/14 | (2006.01) |

(52) U.S. Cl.
CPC ............ *A61B 18/082* (2013.01); *A61B 18/10* (2013.01); *A61B 2018/00404* (2013.01); *A61B 2018/00595* (2013.01); *A61B 2018/00708* (2013.01); *A61B 2018/00922* (2013.01); *A61B 2018/1425* (2013.01); *A61B 2090/309* (2016.02)

(58) Field of Classification Search
CPC ..... A61B 18/12; A61B 18/1206; A61B 18/14; A61B 2018/00922; A61B 2018/00595; A61B 2018/00708
See application file for complete search history.

(56) References Cited

U.S. PATENT DOCUMENTS

| | | |
|---|---|---|
| 4,850,352 A | 7/1989 | Johnson |
| 5,154,709 A | 10/1992 | Johnson |
| 5,195,959 A | 3/1993 | Smith |
| D373,190 S | 8/1996 | Monson |
| 5,674,219 A | 10/1997 | Monson et al. |
| 2002/0087154 A1* | 7/2002 | Shippert ............... A61B 18/082 606/30 |
| 2002/0103485 A1 | 8/2002 | Melynk et al. |
| 2003/0129382 A1* | 7/2003 | Treat ..................... A61B 18/085 428/316.6 |
| 2003/0144656 A1* | 7/2003 | Ocel ....................... A61B 5/042 606/41 |
| 2006/0264928 A1 | 11/2006 | Kornerup et al. |
| 2008/0147058 A1* | 6/2008 | Horrell ............... A61B 18/1402 606/37 |
| 2008/0287893 A1 | 11/2008 | Ineson |
| 2009/0062791 A1 | 3/2009 | Lee et al. |
| 2011/0112530 A1* | 5/2011 | Keller ..................... A61B 18/14 606/42 |
| 2012/0112687 A1* | 5/2012 | Houser ............ A61B 17/00234 320/107 |

* cited by examiner

*Primary Examiner* — Robert N Wieland

(57) ABSTRACT

A blood vessel cauterizing tool assembly includes a housing that has a first end, a second end and a perimeter wall which is attached to and extends between the first and second ends. A cauterizing rod is attached to the housing and extends outwardly away from the first end. A power source is mounted within the housing and is electrically coupled to the cauterizing rod. A switch is mounted on the housing and is operationally coupled to the power source and the cauterizing rod. The switch is actuated to turn the cauterizing rod on or off. A pull tab extends through the perimeter wall and is positioned in a cut off position breaking a circuit between the switch and the power source. The pull tab is removable from the housing to close the circuit.

5 Claims, 4 Drawing Sheets

BLOOD VESSEL CAUTERIZING TOOL ASSEMBLY

BACKGROUND OF THE DISCLOSURE

Field of the Disclosure

The disclosure relates to cauterizing devices and more particularly pertains to a new cauterizing device for allowing a person to cauterize a wound to prevent bleeding.

SUMMARY OF THE DISCLOSURE

An embodiment of the disclosure meets the needs presented above by generally comprising a housing that has a first end, a second end and a perimeter wall which is attached to and extends between the first and second ends. A cauterizing rod is attached to the housing and extends outwardly away from the first end. A power source is mounted within the housing and is electrically coupled to the cauterizing rod. A switch is mounted on the housing and is operationally coupled to the power source and the cauterizing rod. The switch is actuated to turn the cauterizing rod on or off. A pull tab extends through the perimeter wall and is positioned in a cut off position breaking a circuit between the switch and the power source. The pull tab is removable from the housing to close the circuit.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
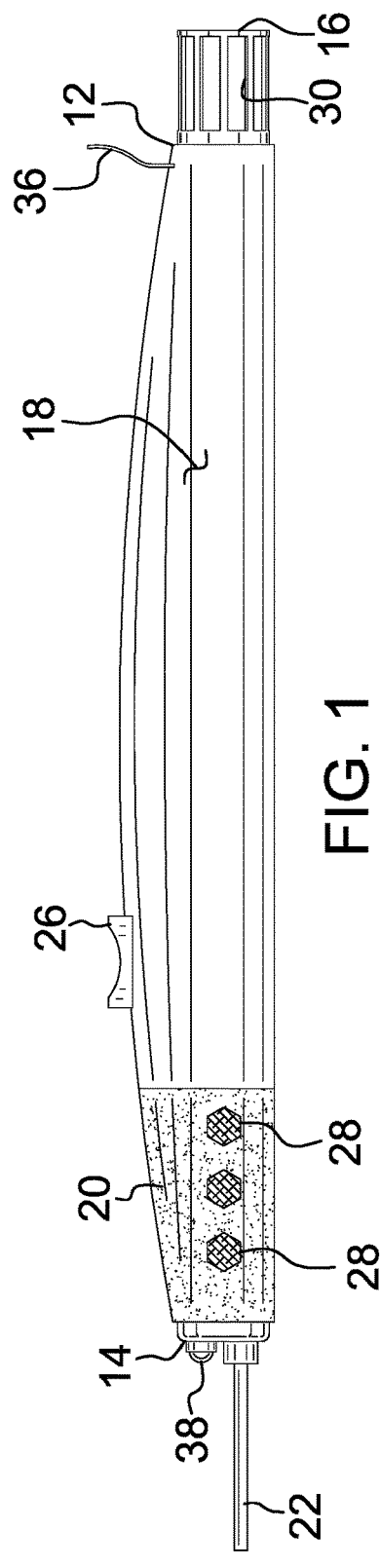
FIG. 1 is a right side view of a blood vessel cauterizing tool assembly according to an embodiment of the disclosure.
Figure 2:
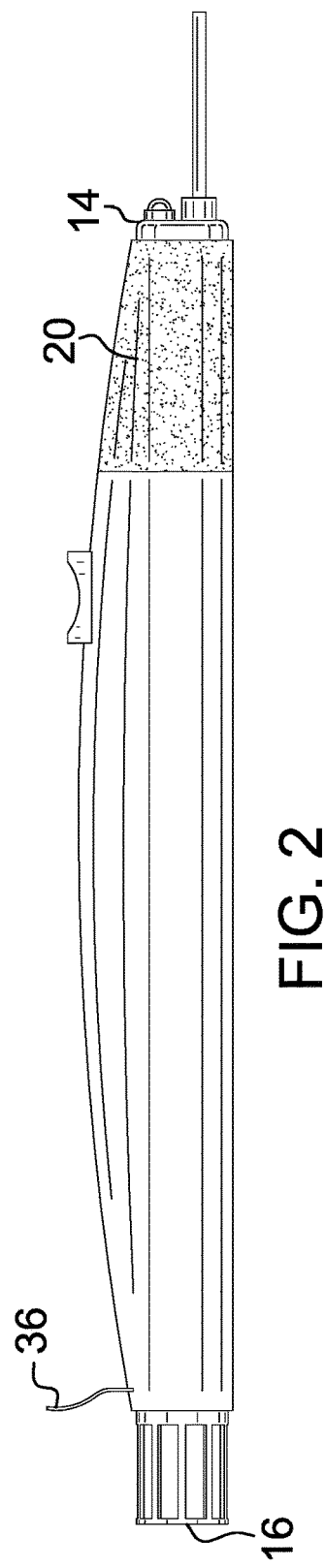
FIG. 2 is a left side view of an embodiment of the disclosure.
Figure 3:
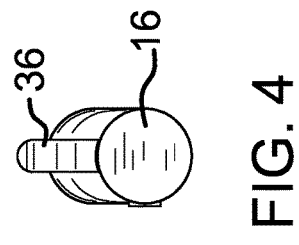
FIG. 3 is a front view of an embodiment of the disclosure.
Figure 4:
FIG. 4 is a rear view of an embodiment of the disclosure.
Figure 5:
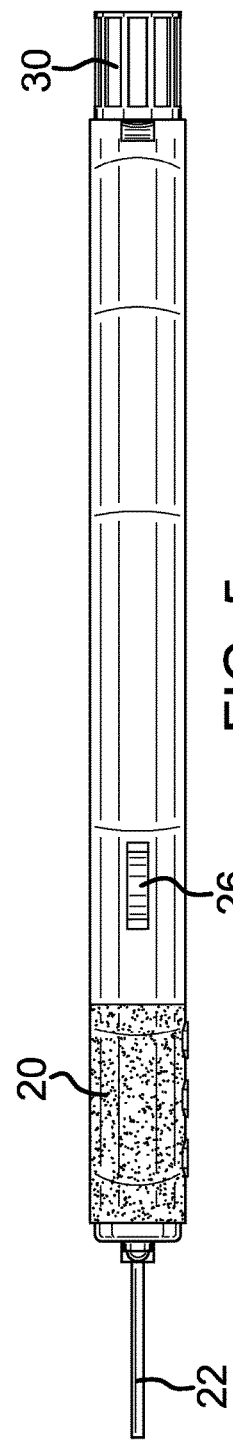
FIG. 5 is a top view of an embodiment of the disclosure.
Figure 6:
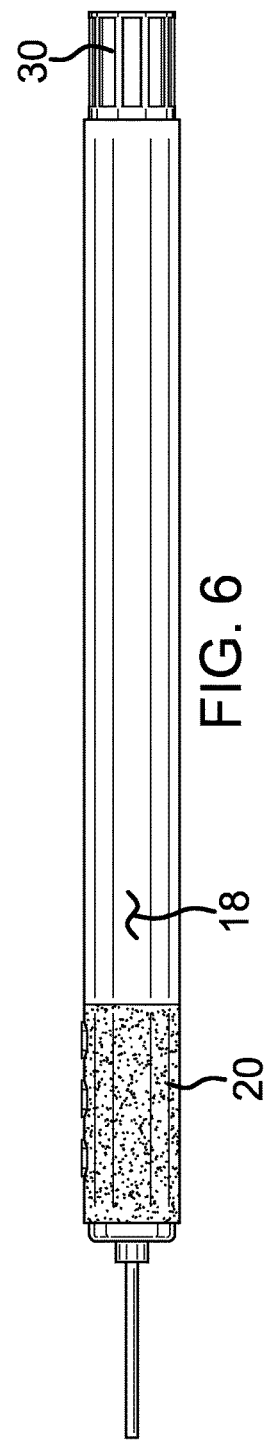
FIG. 6 is a bottom view of an embodiment of the disclosure.
Figure 7:
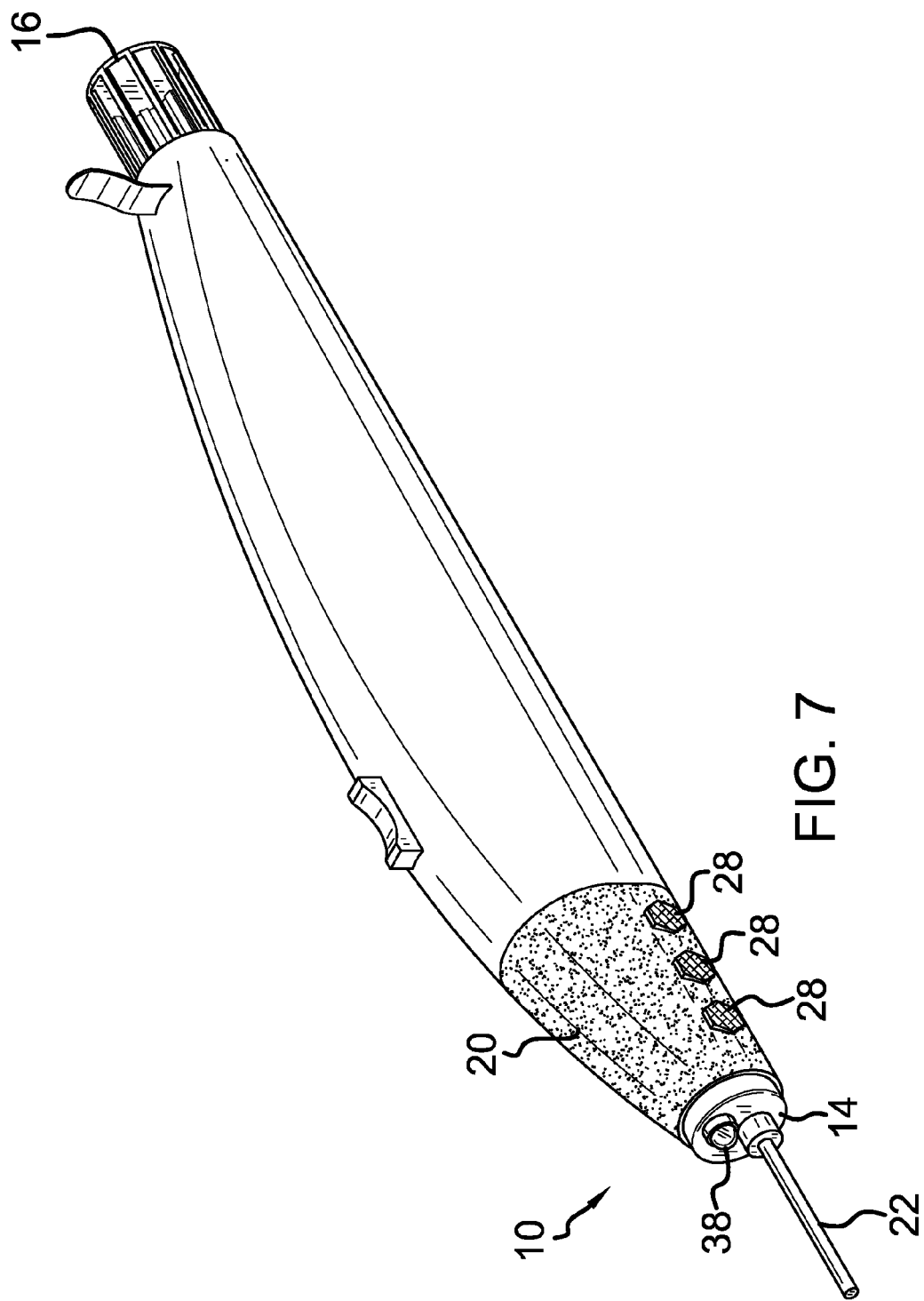
FIG. 7 is a perspective top view of an embodiment of the disclosure.
Figure 8:
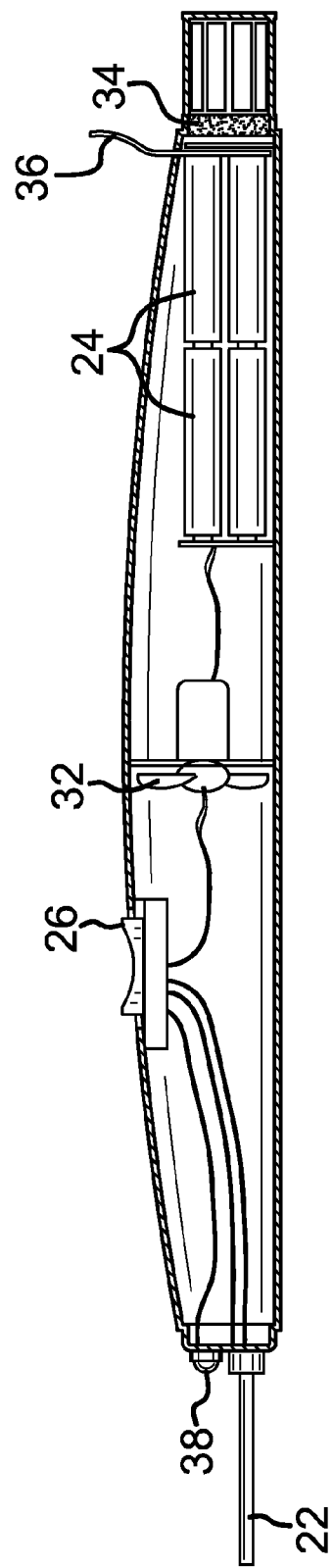
FIG. 8 is a cross-sectional view of an embodiment of the disclosure taken along line 8-8 of FIG. 3.

With reference now to the drawings, and in particular to FIGS. 1 through 8 thereof, a new cauterizing device embodying the principles and concepts of an embodiment of the disclosure and generally designated by the reference numeral 10 will be described.

As best illustrated in FIGS. 1 through 8, the blood vessel cauterizing tool assembly 10 generally comprises a housing 12 having a first end 14, a second end 16 and a perimeter wall 18 that is attached to and extends between the first 14 and second ends 16. The perimeter wall 18 may have a generally cylindrical shape or at least be rounded with a bulbous area centrally located for easy gripping thereof. A non-slip material 20 is positioned on an outer surface of the perimeter wall 18 adjacent to the first end 14. The non-slip material 20 may comprise an elastomer that may or may not have a roughened surface.

A cauterizing rod 22 is attached to the housing 12 and extends outwardly away from the first end 14. A power source 24 is mounted within the housing 12 and is electrically coupled to the cauterizing rod 22. The cauterizing rod 22 may be a conventional electro-cauterizing assembly used for cauterizing wounds and in particular blood vessels and arteries to inhibit loss of blood. The power source 24 may comprise one or more batteries. In this manner the assembly 10 will be portable and may be used outside of a hospital or away from power supplies such as electrical outlets. A switch 26 is mounted on the housing 12 and is operationally coupled to the power source 24 and the cauterizing rod 22. The switch 26 is actuated to turn the cauterizing rod on or off.

The perimeter wall 18 has a plurality of apertures 28 extending therethrough. The apertures 28 are positioned nearer to the first end 14 than the second end 16. The perimeter wall 18 has an opening 30 extending therethrough and there may be a plurality of openings 30 extending through the perimeter wall 18. The openings 30 may be positioned adjacent to the second end 16. A fan 32 is positioned within the housing 12 and is electrically coupled to the power source 24 and to the switch 26 such that the fan 32 is turned on when the switch 26 is actuated to turn on the cauterizing rod 22. The fan 32 draws air into the housing 12 through the apertures 28 and exhausts air outwardly of the housing 12 through the opening 30. A filter 34 is positioned within the housing 12 between the apertures 28 and the opening 30. The filter 34 filters air moving through the housing 12. The filter 34 will remove any noxious fumes from the cauterizing procedure. The filter 34 may be positioned within the apertures 28 as opposed to within the housing 12.

A pull tab 36 may be provided which extends through the perimeter wall 18. The pull tab 36 is positioned in a cut off position breaking a circuit between the switch 26 and the power source 24. The pull tab 36 may for instance be positioned between the batteries and a battery contact to prevent a closed circuit from being formed. The pull tab 36 is removable from the housing 12 to close the circuit. In this way, the cauterizing rod 22 cannot accidentally be powered which would deplete the power source 24 or start a fire or injure someone unaware of the powered nature of the assembly 10.

A light emitter 38 is mounted on the housing 12 and is directed away from the first end 14. The light emitter 38 is electrically coupled to the switch 26 and to the power supply 24. The light emitter 38 is turned on when the switch 26 turns on the cauterizing rod 22. The light emitter 38 may comprise one or more LEDs or alternate forms of light emitters.

In use, the assembly 10 is used in a conventional manner to cauterize wounds. However, the power supply 24 being positioned within the housing 12 allows the assembly 10 to be used in the field, such as in combat situations, where medical personnel and equipment are not available. It should be understood that the assembly 10 may also be used within a hospital setting. The fan 32 and filter 36 will remove air from the area being cauterized to clean and purify the air to reduce inhalation of fumes created during usage of the assembly 10 while the light emitter provides for illumination of a wound.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A cauterizing tool assembly configured to stop bleeding of a wound, said assembly comprising:
    a housing having a first end, a second end and a perimeter wall being attached to and extending between said first and second ends, said perimeter wall having a plurality of apertures extending therethrough, said apertures being positioned nearer to said first end than said second end, said perimeter wall having an opening extending therethrough;
    a cauterizing rod being attached to said housing and extending outwardly away from said first end;
    a power source being mounted within said housing and being electrically coupled to said cauterizing rod;
    a switch being mounted on said housing and being operationally coupled to said power source and said cauterizing rod, said switch being actuated to turn said cauterizing rod on or off;
    a pull tab extending through said perimeter wall, said pull tab being positioned in a cut off position breaking a circuit between said switch and said power source, said pull tab being removable from said housing to close the circuit;
    a fan being positioned within said housing, said fan being electrically coupled to said power source and to said switch, said fan being turned on when said switch is actuated to turn said cauterizing rod on, said fan drawing air into said housing through said apertures and exhausting air outwardly of said housing through said opening; and
    a filter being positioned within said housing between said apertures and said opening, said filter filtering air moving through said housing.

2. The cauterizing tool assembly according to claim 1, further including a non-slip material being positioned on an outer surface of said perimeter wall adjacent to said first end.

3. A cauterizing tool assembly configured to stop bleeding of a wound, said assembly comprising:
    a housing having a first end, a second end a perimeter wall being attached to and extending between said first and second ends;
    a cauterizing rod being attached to said housing and extending outwardly away from said first end;
    a power source being mounted within said housing and being electrically coupled to said cauterizing rod;
    a switch being mounted on said housing and being operationally coupled to said power source and said cauterizing rod, said switch being actuated to turn said cauterizing rod on or off;
    said perimeter wall having a plurality of apertures extending therethrough, said apertures being positioned nearer to said first end than said second end;
    said perimeter wall having an opening extending therethrough; and
    a fan being positioned within said housing, said fan being electrically coupled to said power source and to said switch, said fan being turned on said switch is actuated to turn said cauterizing rod on, said fan drawing air into said housing through said apertures and exhausting air outwardly of said housing through said opening.

4. The cauterizing tool assembly according to claim 3, further including a non-slip material being positioned on an outer surface of said perimeter wall adjacent to said first end.

5. A cauterizing tool assembly configured to stop bleeding of a wound, said assembly comprising:
    a housing having a first end, a second end and a perimeter wall being attached to and extending between said first and second ends;
    a cauterizing rod being attached to said housing and extending outwardly away from said first end;
    a power source being mounted within said housing and being electrically coupled to said cauterizing rod;
    a switch being mounted on said housing and being operationally coupled to said power source and said cauterizing rod, said switch being actuated to turn said cauterizing rod on or off;
    said perimeter wall having a plurality of apertures extending therethrough, said apertures being positioned nearer to said first end than said second end;
    said perimeter wall having an opening extending therethrough;
    a fan being positioned within said housing, said fan being electrically coupled to said power source and to said switch, said fan being turned on when said switch is actuated to turn said cauterizing rod on, said fan drawing air into said housing through said apertures and exhausting air outwardly of said housing through said opening;
    a filter being positioned within said housing between said apertures and said opening, said filter filtering air moving through said housing;
    a pull tab extending through said perimeter wall, said pull tab being positioned in a cut off position breaking a circuit between said switch and said power source, said pull tab being removable from said housing to close the circuit;
    a non-slip material being positioned on an outer surface of said perimeter wall adjacent to said first end; and
    a light emitter being mounted on said housing and being directed away from said first end, said light emitter being electrically coupled to said switch and to said power supply, said light emitter being turned on when said switch turns on said cauterizing rod.

\* \* \* \* \*